United States Patent
Kolahi et al.

(10) Patent No.: US 9,207,212 B2
(45) Date of Patent: Dec. 8, 2015

(54) METHOD FOR OPERATING A RESONANT MEASUREMENT SYSTEM

(71) Applicant: KROHNE Messtechnik GmbH, Duisburg (DE)

(72) Inventors: Kourosh Kolahi, Duisburg (DE); Ralf Storm, Essen (DE); Andreas Poremba, Wuppertal (DE)

(73) Assignee: Krohne Messtechnik GmbH, Duisburg (DE)

( * ) Notice: Subject to any disclaimer, the term of this patent is extended or adjusted under 35 U.S.C. 154(b) by 0 days.

(21) Appl. No.: 14/409,160

(22) PCT Filed: Jun. 18, 2013

(86) PCT No.: PCT/EP2013/001792
§ 371 (c)(1),
(2) Date: Dec. 18, 2014

(87) PCT Pub. No.: WO2013/189589
PCT Pub. Date: Dec. 27, 2013

(65) Prior Publication Data
US 2015/0177192 A1    Jun. 25, 2015

(30) Foreign Application Priority Data

Jun. 18, 2012  (DE) .................. 10 2012 011 934
Jun. 18, 2012  (DE) .................. 10 2012 011 935

(51) Int. Cl.
*G01F 1/84* (2006.01)
*G01N 29/036* (2006.01)
*G01F 1/66* (2006.01)

(52) U.S. Cl.
CPC .............. *G01N 29/036* (2013.01); *G01F 1/662* (2013.01); *G01F 1/8422* (2013.01); *G01F 1/8431* (2013.01); *G01F 1/8468* (2013.01); *G01F 1/8436* (2013.01)

(58) Field of Classification Search
CPC .......................................................... G01F 3/84
USPC ...................................... 73/861.355–861.357
See application file for complete search history.

(56) References Cited

U.S. PATENT DOCUMENTS

| | | | |
|---|---|---|---|
| 7,404,336 B2 | 7/2008 | Henry et al. | |
| 7,412,903 B2 * | 8/2008 | Rieder .................. | G01F 1/8409 73/861.355 |
| 8,104,361 B2 | 1/2012 | Kolahi | |

(Continued)

FOREIGN PATENT DOCUMENTS

WO    2008/003629 A1    1/2008

*Primary Examiner* — Jewel V Thompson
(74) *Attorney, Agent, or Firm* — Roberts Mlotkowski Safran & Cole, PC

(57) ABSTRACT

Method for operating a resonant measurement system, especially a Coriolis mass flow meter, so as to be excitable in a linear operating range, the driving terminal current triggered by an electric excitation signal and the driving terminal voltage of the electromagnetic drive triggered by the electric excitation signal are measured. The driving power is determined from the driving terminal current and the driving terminal voltage, and if the driving terminal current exceeds a given maximum driving terminal current, and/or if the driving terminal voltage exceeds a given maximum driving terminal voltage and/or if the driving power exceeds a given maximum driving power, the electric excitation signal is limited to a threshold value such that the driving terminal current remains below the given maximum driving terminal current, and/or the driving terminal voltage remains below the given maximum driving terminal voltage, and/or the driving power remains below the maximum driving power.

8 Claims, 6 Drawing Sheets

(56) References Cited

U.S. PATENT DOCUMENTS

| | | | |
|---|---|---|---|
| 8,593,838 B2 | 11/2013 | Poremba et al. | |
| 8,950,274 B2 * | 2/2015 | Scherrer | G01F 1/66 702/45 |
| 2002/0133307 A1 * | 9/2002 | Maginnis | G01F 1/8418 702/100 |
| 2013/0199306 A1 | 8/2013 | Kolahi et al. | |
| 2013/0338943 A1 | 12/2013 | Kolahi et al. | |

* cited by examiner

METHOD FOR OPERATING A RESONANT MEASUREMENT SYSTEM

BACKGROUND OF THE INVENTION

1. Field of the Invention

The invention relates to a method for operating a resonance measurement system, especially a Coriolis mass flow meter, the resonance measurement system comprising at least one electrical actuating apparatus, at least one electromagnetic drive as a vibration generator and at least one vibrating element which interacts with a medium, the electrical actuating apparatus making available an electrical excitation signal for excitation of the electromagnetic drive and the electromagnetic drive exciting the vibrating element to vibration in at least one natural form.

2. Description of Related Art

Resonance measurement systems of the aforementioned type have been known for years, not only in the form of Coriolis mass flow meters, but also as density measuring instruments or level detectors according to the tuning fork principle, as quartz carriages and belt viscosimeters. These resonance measurement systems are connected to a process/process medium, the process and process medium and resonance measurement system mutually influencing one another.

Resonance measurement systems are treated below using the example of Coriolis mass flow meters; this is not to be understood as limiting. It is irrelevant whether they are Coriolis mass flow meters with one or several measuring tubes, with straight or bent measuring tubes. Here, quite generally, those systems in which information about the process variables (measured variables) to be determined are encoded in the natural frequencies and/or those systems in which working points are placed at the natural frequencies of the measurement system are called resonance measurement systems. What is stated below can be applied to all systems which fall under this definition. In Coriolis mass flow meters, the measuring tube corresponds to the vibrating element of the resonance measurement system; this special configuration of the vibrating element does not constitute a limitation for the teaching which can be applied in general to resonance measurement systems either.

Resonance measurement systems which are made as Coriolis mass flow meters are used mainly in industrial process measurement engineering, where mass flows must be determined with high precision. The manner of operation of Coriolis mass flow meters is based on at least one measuring tube through which a medium flows—the vibrating element—being excited to vibration by a vibration generator, this vibration generator being an electromagnetic drive. In this electromagnetic drive, conventionally, an electric current flows through a coil, the action of a force on the vibrating element being linked directly to the coil current. In Coriolis mass flow meters, the manner of operation is based on the mass-burdened medium reacting on the wall of the measuring tube as a result of the Coriolis inertial force which has been caused by two orthogonal movements, that of the flow and that of the measuring tube. This reaction of the medium on the measuring tube leads to a change of the measuring tube vibration compared to the vibration state of the measuring tube in the absence of flow through it. The mass flow rate through the measuring tube can be determined with high precision by detecting these particulars of the vibrations of the Coriolis measuring tube which has been exposed to flow through it.

The natural frequencies of the Coriolis mass flow meter or the resonant parts of the Coriolis mass flow meter, essentially therefore the natural frequencies of the measuring tube as the vibrating element, are of special importance, because the working points of the Coriolis mass flow meters are conventionally placed on natural frequencies of the measuring tube in order to be able to impress the necessary vibrations for the induction of the Coriolis forces with a minimum energy expenditure. The vibrations which are then executed by the measuring tube have a certain mode which is called the natural mode of the respective excitation. Another reason for the special importance of natural frequencies in Coriolis mass flow meters is the direct physical linkage between the natural frequency of the measuring tube which has been exposed to flow through it and the effectively deflected vibrating mass (measuring tube and mass of the medium in the measuring tube); the density of the medium can be determined via this relationship.

It is known from the prior art that, in order to excite the vibrating element by a controller, a harmonic base signal as the controller output signal is generated in the form of a sinusoidal voltage and this sinusoidal voltage triggers the electrical actuating apparatus, the electrical actuating apparatus being designed to make available a corresponding power at its output in order to be able to trigger the electromagnetic drive in a suitable manner and with sufficient power; the electrical actuating apparatus is thus essentially the power link between the controller and the electromagnetic drive of the resonance measurement system. Usually known Coriolis mass flow meters are also equipped with a vibration sensor, since in the vibration of the vibrating element which is interacting with a medium usually there is physical information of interest about the medium, for example, the flow rate, the density and the viscosity.

In resonance measurement systems in industrial practice, the available electric power is often limited for different reasons. One reason for this limitation can be, for example, that the resonance measurement system is designed for the type of protection "intrinsic safety". This yields manipulated variable limitations which lead to limitations of the electrical excitation signal and thus to nonlinearities when approaching and holding predetermined working points.

The invention is based on the finding that the nonlinearities which are caused for example, by limitations of manipulated variables lead to unwanted multi-frequency excitations of the resonance measurement system. For example, the load on the resonance measurement system when measuring multiphase flows or highly viscous materials is so great that limits in the drive chain and especially in the electrical actuating apparatus become active. In this way the resonance measurement system is excited not only at predetermined frequencies, but also at many unwanted frequencies. This changes the working point (vibration mode) and thus also the properties of the resonance measurement system such as the zero point and the sensitivity; it increases the measurement noise, reduces the accuracy of the evaluation of the measurement signals and increases the measurement uncertainty of the measured values.

Another problem with respect to the power consumption of the resonance measurement system, and thus, also to the level of the electrical excitation signals can be that the resonance measurement system is to be operated in different predetermined operating modes, in which certain modules have a large power demand so that "normal" measurement operation cannot be maintained for reasons of power technology. For example, the power demand in a diagnosis operation of the vibrating element can be so high that the driving power must be reduced for measurement operation.

To influence the power consumption, executing certain functions of the resonance measurement system only in sequence so that the instantaneous power demand does not exceed a predetermined quantity is known. For example, the driving of the measuring tubes of a Coriolis mass flow meter can be discontinued when sending the measurement data; this is important for example, in two-lead resonance measurement systems.

In many resonance measurement systems which are known from the prior art, the power limitation, and thus, also the manipulated variable limitation are simply ignored. But, this procedure leads to undefined states of the resonance measurement system, and thus, to major measurement uncertainties. An undefined state is present, for example, if the vibrating element is also excited with signals of unknown frequency in unintended natural modes in addition to known and intended excitations. As a result, the predetermined working point becomes uncertain; for example, in a Coriolis mass flow meter, the intended defined change in the momentum of the flowing mass particles is not possible.

Uncertainties in the working point then also cause model uncertainties in the evaluation of the response signals of the vibrating element, and thus, also further measurement uncertainties in the measurement results.

SUMMARY OF THE INVENTION

Therefore, the object of this invention is to devise a method for operating a resonance measurement system in which operation of the resonance measurement system in the linear range is also ensured when boundary conditions and power requirements change.

The aforementioned object is achieved in the aforementioned known method in that the driving terminal current $i_{DrA}$ caused by the electrical excitation signal $u_2$ and the driving terminal voltage $u_{DrA}$ of the electromagnetic drive caused by the electrical excitation signal $u_2$ are detected by measurement, the driving power $S_{DrA}$ is determined from the driving terminal current $i_{DrA}$ and driving terminal voltage $u_{DrA}$, when a given maximum driving terminal current $i_{DrA-max}$ is exceeded by the driving terminal current $i_{DrA}$ and/or when a given maximum driving terminal voltage $U_{DrA-max}$ is exceeded by the driving terminal voltage $u_{DrA}$, and/or when a given maximum driving power $S_{DrA-max}$ is exceeded by the driving power $S_{DrA}$, the electrical excitation signal $u_2$ is limited to a limit value $u_{2-B}$ such that the driving terminal current $i_{DrA}$ remains below the given maximum driving terminal current $i_{DrA-max}$ and/or the driving terminal voltage $u_{DrA}$ remains below the given maximum driving terminal voltage $u_{DrA-max}$ and/or the driving power $S_{DrA}$ remains below the maximum driving power $S_{DrA-max}$.

The idea which underlies the method in accordance with the invention is therefore based, first of all, on the measurement engineering detection of the terminal variables of the electromagnetic drive which impart an impression of the load situation of the resonance measurement system, in the case of a Coriolis mass flow meter which also impart an impression of the loading of the electromagnetic drive itself (coil, permanent magnet and eddy currents), the measuring tubes and the medium which is flowing through the measuring tubes. The terminal variables of the electromagnetic drive render how the electrical actuating apparatus is electrically loaded. The continuing measurement of the driving terminal voltage $u_{DrA}$ and of the driving terminal current $i_{DrA}$ fundamentally makes it possible to detect an also variable load behavior of the resonance measurement system.

As soon as it is recognized that the resonance measurement system has moved into a boundary state, therefore the driving terminal current $i_{DrA}$ exceeds a given maximum driving terminal current $i_{DrA-max}$ or the driving terminal voltage $u_{DrA}$ exceeds a given maximum driving terminal voltage $u_{DrA-max}$ or the instantaneous driving power $S_{DrA}$ exceeds the given maximum driving power $S_{DrA-max}$, the excitation signal $u_2$ is limited to a limit value $u_{2-B}$ so that the driving terminal variables or the driving power are not exceeded. Reducing the electrical excitation signal $u_2$ therefore prevents one of the actual boundaries from being reached.

In one preferred configuration of the method, it is provided that from the measured driving terminal current $i_{DrA}$ and from the measured driving terminal voltage $u_{DrA}$, the complex load admittance G or the complex load resistance Z with which the electrical actuating apparatus is loaded is determined, and that the limit value $u_{2-B}$ for the electrical excitation signal is determined based on the complex load admittance G and/or based on the complex load resistance Z. By temporal measurement of the driving terminal current $i_{DrA}$ and the driving terminal voltage $u_{DrA}$ the load admittance G or the load resistance Z can be determined in amount and phase, in other words, the complex load admittance G or the complex load resistance Z can be determined; this is of interest for the conventional case of the harmonic excitation of the resonance measurement system.

In one special configuration of the method, it is provided that the limitation of the electrical excitation signal $u_2$ to the limit value $u_{2-B}$ takes place by a matched, especially smaller set point for the amplitude being stipulated for an amplitude adjustment for adjusting the amplitude of the vibrating element.

In particular, there are now various possibilities for embodying and developing the method in accordance with the invention as will be apparent from the following description of preferred exemplary embodiments in conjunction with the accompanying drawings.

DETAILED DESCRIPTION OF THE INVENTION

Figure 4:
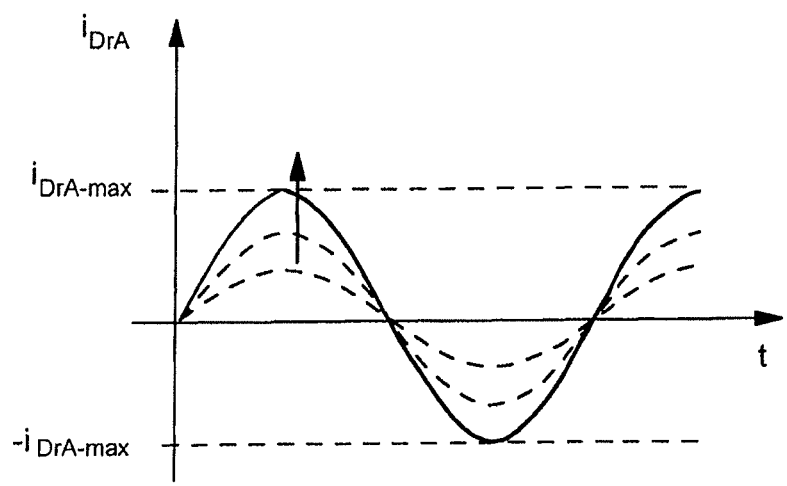
FIG. 4 shows the desired linear operation of a resonance measurement system which is achieved when using the method in accordance with the invention, FIG. 5 schematically shows the structure of a resonance measurement system in the form of a Coriolis mass flow meter as is known from the prior art, but as can also be used for the method in accordance with the invention.
Figure 5:
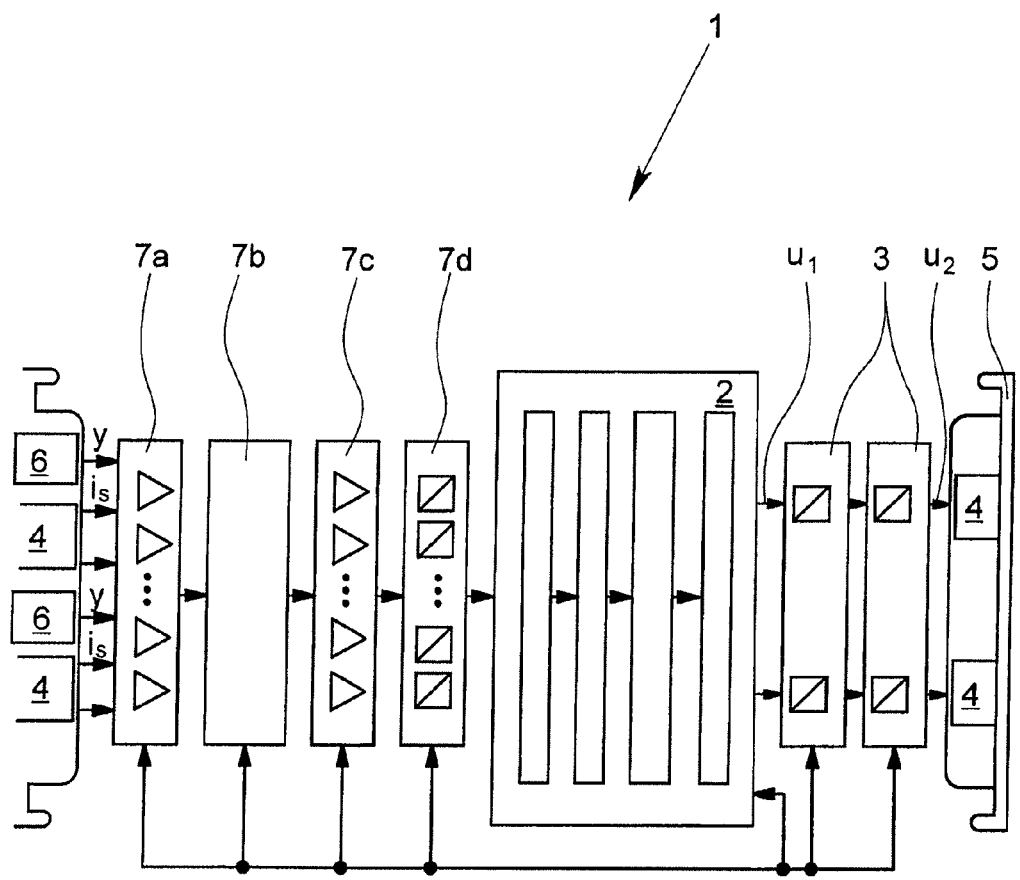

FIG. 5 shows, first of all, a resonance measurement system 1 which is operated with the method of the invention which is explained in detail below. Using FIG. 5, this resonance measurement system 1 will first be explained before different operating situations of the resonance measurement system which are the subject matter of FIGS. 1 to 4 are explained.

FIG. 5 shows a resonance measurement system 1 in the form of a Coriolis mass flow meter, the resonance measurement system 1 having a controller 2 which has been implemented in a signal processor, an electrical actuating apparatus 3 and an electromagnetic drive 4 as a vibration generator.

The electromagnetic drive 4 is designed to excite a vibrating element 5, here a measuring tube through which a medium can flow, to a vibration in a natural mode. Depending on the type of natural mode, to do this, only one individual electromagnetic drive 4 is necessary; if higher modes are also to be excited, two or more electromagnetic drives 4 can also be necessary. This is not important to the method described below for operating the resonance measurement system 1.

FIG. 5 shows the resonance measurement system 1 in the form of the Coriolis mass flow meter in two parts. The Coriolis mass flow meter, which actually forms a unit, is shown for reasons of clarity with one half of the vibrating element 5 on the right edge of the figure and with the other half of the vibrating element 5 on the left edge of the figure. In the figure, it can be recognized that the resonance measurement system 1 also has vibration sensors 6 which output an output signal y, here in the form of a velocity signal y, which yields information about the velocity of the movement of the measuring tube, therefore of the vibrating element 5. The vibration sensor 6 is not critically necessary for carrying out the method described below. The vibration sensor 6 is connected to a plurality of transmission elements which are used essentially for signal conditioning, such as, for example, matching electronics 7a comprised of amplifiers, a hardware multiplexer 7b for implementing different switchable measurement channels, further matching electronics 7c and an analog/digital converter 7d which again supplies the analog measured signals to the controller 2 in the form of digital signals. The controller 2 generates a controller output signal $u_1$ for triggering the electrical actuating apparatus 3, and the electrical actuating apparatus 3 subsequently generates an electrical excitation signal $u_2$ for excitation of the electromagnetic drive 4.

Various methods are known in which a mathematical model 8 of the resonance measurement system 1, which maps at least the vibrating element 5, is set up and parameters of the mathematical model 8 are identified by suitable excitations of the vibrating element 5 and evaluation of the mathematical model 8 and the identified parameters and/or quantities which have been derived from them are used for operating the resonance measurement system 1. The mathematical model 8 is shown in FIG. 5 as a component of the controller 2, all methods for operating the Coriolis mass flow meter being implemented essentially in the form of programs on one or more computer units. Working with mathematical models 8 is not the subject matter of this application, but rather is explained in other applications, such as for example, German Patent Application DE 10 2011 012 498 A1 and corresponding U.S. Patent Application Publication U.S. 2013/0199306 A1 (multiphase detection) or German Patent Application DE 10 2008 059 920 A1 and corresponding U.S. Pat. No. 8,104, 361 B2 (selective parameter identification). An extensive mathematical model 8 is not required either for implementation of the method treated here. Rather, the method can be quantitatively implemented, for example, using quite simple physical relationships; this is also explained below.

Figure 1:
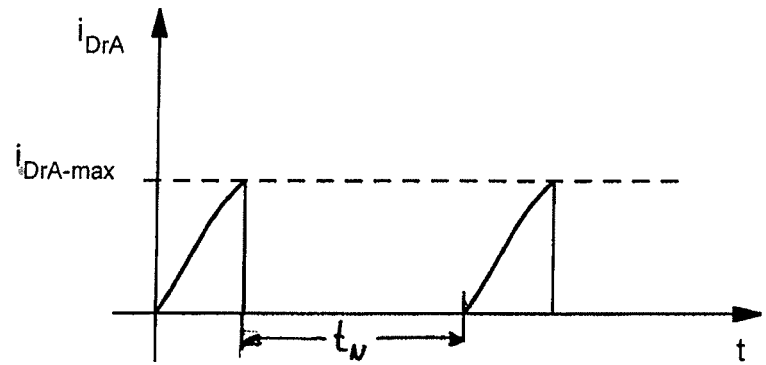
FIG. 1 shows a first example for a nonlinear excitation of a resonance measurement system.
Figure 2:
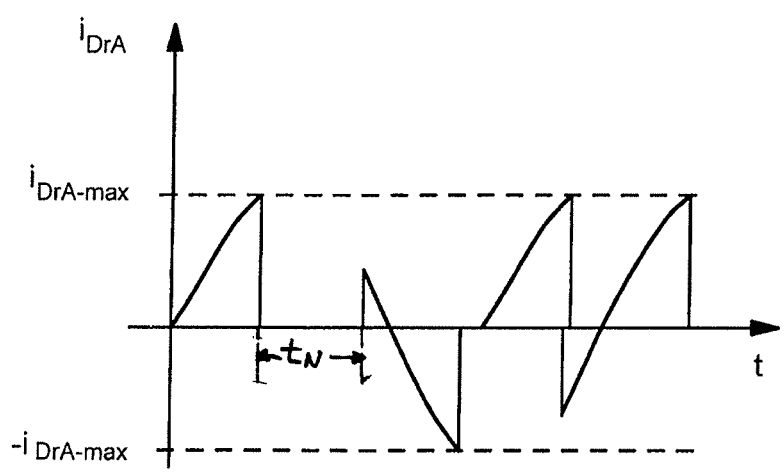
FIG. 2 shows another example for the nonlinear operation of a resonance measurement system.
Figure 3:
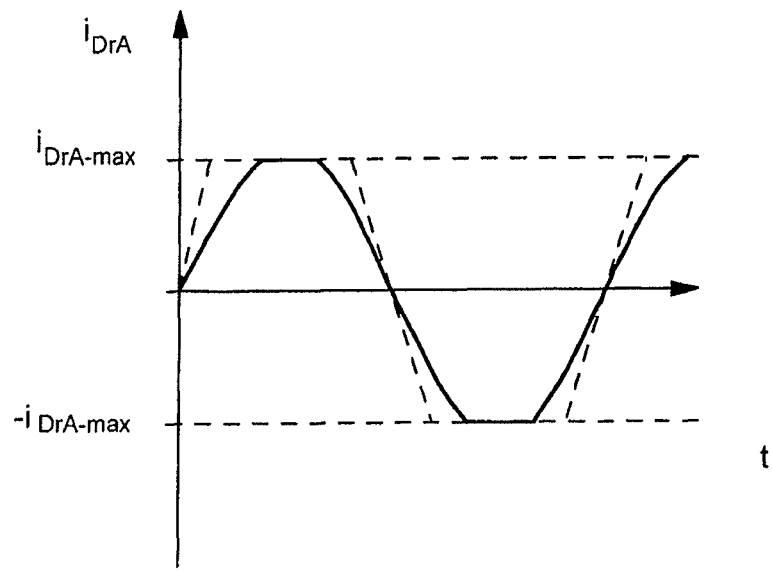
FIG. 3 shows another example for the nonlinear excitation of a resonance measurement system.

FIGS. 1 to 3 show different situations which are to be avoided with the use of the method in accordance with the invention. FIG. 1 shows the characteristics of the driving terminal current $i_{DrA}$ over time, $i_{DrA-max}$ designating a given maximum driving terminal current and constituting a threshold value for this current. The current characteristic $i_{DrA}$ is shown when, for example, ex-disconnection—in implementing the type of protection "intrinsic safety"-becomes active. This can be the case when the predetermined maximum values of the driving power $S_{DrA-max}$, of the driving terminal current $i_{DrA-max}$ or of the driving terminal voltage $u_{DrA-max}$ are exceeded. In this case, the hardware of the resonance measurement system 1 is turned off ("crash"). This case is shown in FIG. 1 for the driving terminal current $i_{DrA}$. After a time-consuming restart, the measurement system may repeatedly crash if the cause, high loading of the vibrating element, is not taken into account. The measurement system in this operating state can, of course, not supply any information about the process variable. Moreover, during the restart phase $t_N$, no communication with the measurement system is possible so that no diagnosis data are available.

FIG. 2 shows a further undefined state of the resonance measurement system 1 when the electrical excitation signal $u_2$ is turned off as a result of a predetermined limit being exceeded or undershot—$i_{DrA-max}$ for the driving terminal current and $u_{DrA-max}$ for the driving terminal voltage. The excitation signal is turned on again after a predetermined waiting time $t_N$. Since this waiting time is independent of the loading of the vibrating element 5, unintended, and thus, uncontrolled excitation may occur which excites the vibrating element 5 with unknown frequencies in several natural frequencies. But, the working point of the vibrating element 5 is thus unknown and is not quasi-steady state. Thus, the response signals of the vibrating element 5 can only be evaluated with difficulty, for example, because the evaluation is based on a mathematical model 8 which works more or less quasi-steady state. As a result, this error leads to measurement uncertainties in the measurement results.

An undefined state or working behavior with strong non-linearities also occurs when, as shown in FIG. 3, the electrical excitation signal $u_2$ is limited to predetermined maximum values. In the example of FIG. 3, here, it is the driving terminal current $i_{DrA}$ which is limited to a given maximum driving terminal current $i_{DrA-max}$ for positive values as for negative values. In this case, the excitation of a harmonic excitation at low load on the vibrating element passes into a rectangular excitation—broken line, capped sine curve—at high load. In this way, as in the above described cases in FIGS. 1 and 2, the working point becomes uncertain, and thus, the measurement uncertainty of the measurement results also rises.

To avoid the uncontrolled operating situations shown above using FIGS. 1 to 3 with the large-scale occurrence of nonlinearities, in accordance with the invention, for the operation of the resonance measurement system 1, it is now provided that the driving terminal current $i_{DrA}$ which has been caused by the electrical excitation signal $u_2$ and the driving terminal voltage $u_{DrA}$ of the electromagnetic drive 4 which has been caused by the electrical excitation signal $u_2$ are detected by measurement, the driving power $S_{DrA}$ is determined from the driving terminal current $i_{DrA}$ and the driving terminal voltage $u_{DrA}$, when a given maximum driving terminal current $i_{DrA-max}$ is exceeded by the driving terminal current $i_{DrA}$ and/or when a given maximum driving terminal voltage $u_{DrA-max}$ is exceeded by the driving terminal voltage $u_{DrA}$, and/or when a given maximum driving power $S_{DrA-max}$ is exceeded by the driving power $S_{DrA}$, the electrical excitation signal $u_2$ is limited to a limit value $u_{2-B}$ such that the driving terminal current $i_{DrA}$ remains below the given maximum driving terminal current $i_{DrA-max}$ and/or the driving terminal voltage $u_{DrA}$ remains below the given maximum driving terminal voltage $u_{DrA\text{-}max}$ and/or the driving power $S_{DrA}$ remains below the maximum driving power $S_{DrA\text{-}max}$.

The described limitation of the electrical excitation signal $u_2$ to the limit value $u_{2\text{-}B}$ results in that the excitation of the resonance measurement system or of the vibration generator in the form of the measuring tubes of a Coriolis mass flow meter is limited such that excitation always takes place with harmonic excitation, therefore linear operating behavior can be maintained. The operating behavior of the resonance measurement system 1 which is caused with the described method is shown in FIG. 4, the arrow indicated there pointing in the direction of increasing load of the electromagnetic drive 4 by the vibration generator. As a result, in any case, it must be recognized that the electrical excitation signal $u_2$ is computed and stipulated depending on the electrical load such that, on the one hand, the excitation signal, here in the form of the driving terminal current $i_{DrA}$, remains harmonic, and on the other hand, none of the predetermined extreme values $S_{DrA\text{-}max}$ for the driving power, $i_{DrA\text{-}max}$ for the driving terminal current and $u_{DrA\text{-}max}$ for the driving terminal voltage are exceeded. The electrical input variables of the resonance measurement system 1, therefore the driving terminal current $i_{DrA}$, the driving terminal voltage $u_{DrA}$ and the driving power $S_{DrA}$, and thus, the loading of the resonance measurement system 1, are measured by the process and the set points for the working points and/or the manipulated variable limitation are set and pre-computed such that the components of the resonance measurement system 1 always operate in the linear range, and as much as possible, the resonance measurement system 1 need not be turned off at high load. The proposed method sets the set points and/or manipulated variable limitations as a function of the current loading of the resonance measurement system 1 and as a function of the available power such that all relevant components and units in the driving and measuring chain work in the linear region.

Figure 6:
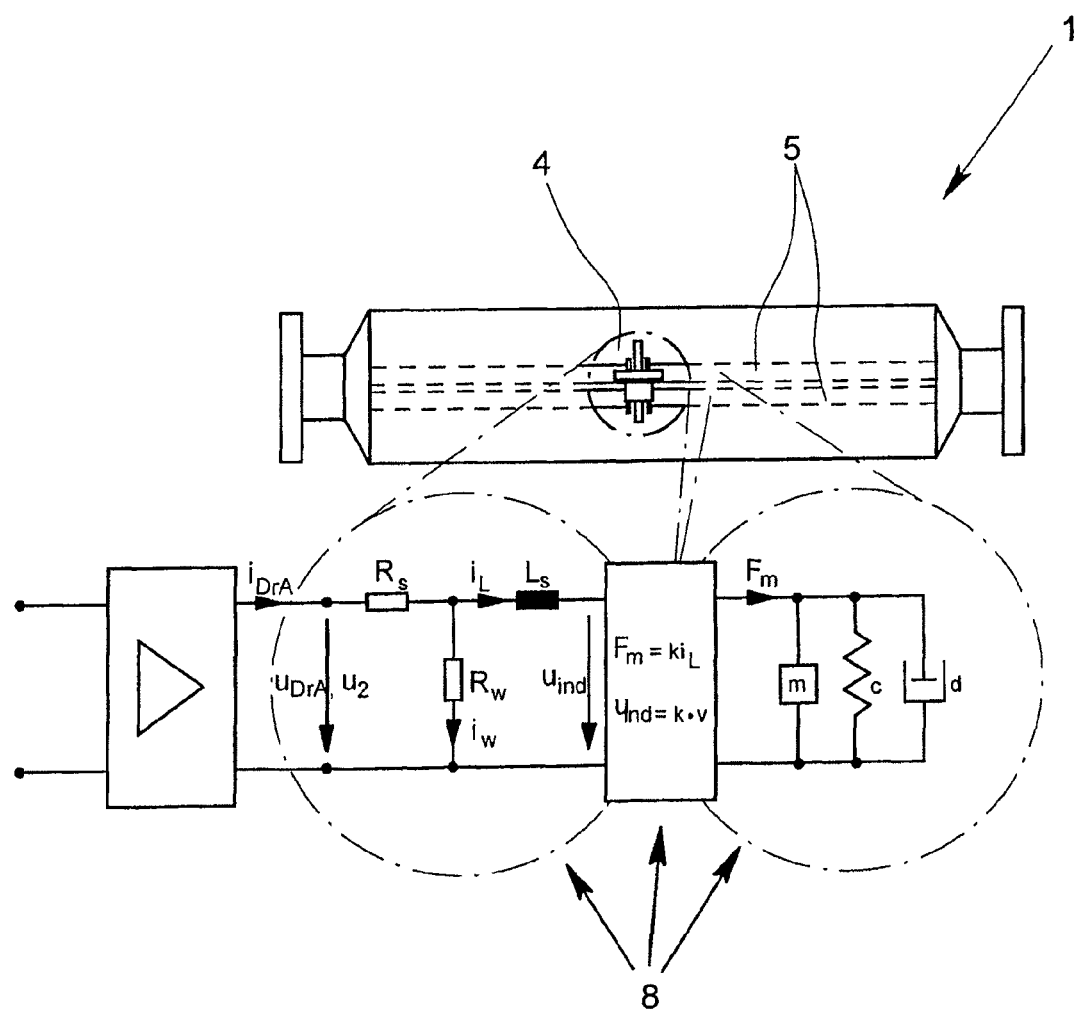
FIG. 6 shows the equivalent circuit diagram of the mathematical model of an electromagnetic drive and of a coupled vibrating element in the form of a measuring tube.

To better understand the relationships, FIG. 6 shows the physical relationships in a resonance measurement system 1 a mathematical model 8 in the form of an equivalent circuit diagram; this mathematical model 8 itself is not needed to carry out the method of the invention. In the upper section of FIG. 6, first a Coriolis mass flow meter is shown as the resonance measurement system 1, two measuring tubes being indicated as the vibrating element 5. Furthermore, an electromagnetic drive 4 is suggested with which the measuring tubes can be deflected relative to one another, and thus, are excited to vibration. In the lower part of FIG. 6, an equivalent circuit diagram is shown for the electromagnetic drive 4—left side— and for the vibrating element 5 which interacts with the medium—right side. Furthermore, it is shown that the electrical actuating apparatus 3 produces an electrical excitation signal $u_2$ for excitation of the electromagnetic drive 4.

The driving terminal current $i_{DrA}$ which has been caused by the electrical excitation signal $u_2$ and the driving terminal voltage $u_{DrA}$ of the electromagnetic drive 4 which has been caused by the electrical excitation signal $u_2$ are acquired by measurements; this is not shown in particular here. The electrical excitation signal $u_2$ can be the driving terminal voltage $u_{DrA}$ or the driving terminal current $i_{DrA}$; the letter "u" which is used therefore does not necessarily indicate a voltage. The driving terminal current $i_{DrA}$ can be tapped, for example, by the voltage drop on an ohmic resistance, the driving terminal voltage $u_{DrA}$ can be tapped in a high-resistance manner directly by an analog measurement input of a digital signal processor or can be digitized by a separate analog-digital converter.

The mathematical model 8 shown here thus also maps the physical properties of the electromagnetic drive 4 so that effects of the electromagnetic drive 4 can also be included in the calculation. In this case, the parameters of the electromagnetic drive 4 and of the vibrating element 5 are, for example, specified, but they can also be determined by suitable identification methods, in this respect see commonly owned co-pending U.S. Patent Application Publication 2013/0338943, which is hereby incorporated by reference to the extent necessary to complete an understanding of the present invention. However, the manner in which the parameters can be determined is not the subject matter of this application.

It is apparent from the model concept shown in FIG. 6 that the mathematical model 8 maps the electromagnetic drive 4 and the vibrating element 5 which interacts with the medium altogether as the load of the electrical actuating apparatus 3, the load corresponding to the ratio of the driving terminal voltage $u_{DrA}$ and the driving terminal current $i_{DrA}$. The following applies:

$$Z(j\omega) = \frac{U_{DrA}(j\omega)}{I_{DrA}(j\omega)}. \tag{1}$$

In the aforementioned equation description, it is assumed that the electrical excitation signal $u_2$ is a harmonic excitation signal so that the complex-valued formulation offers itself. It becomes clear in the examination of FIG. 6 that the complex load resistance is altogether dependent on the properties of the vibration generator 4 (inductance of the coil, ohmic resistance of the coil, and eddy current losses), on the mechanical properties of the vibrating element 5 in the form of measuring tubes and also on the properties of the medium which interacts with the vibrating element 5, here on the medium which is flowing through the measuring tubes. The complex load resistance is therefore dependent on the electrical, mechanical and flow-mechanical properties of the electromagnetic drive 4 and of the vibrating element 5 which interacts with the medium.

In the equivalent circuit diagram shown in FIG. 6, the substitute quantities altogether have the following meaning:
$u_{DrA}$=voltage at the output of the power amplifier (voltage on the driving coil),
$i_{DrA}$=current at the output of the power amplifier (current through the driving coil),
$i_L$=current through the equivalent inductance,
k=transfer coefficient,
$R_S$=ohmic resistance of the driving coil,
$R_W$=eddy current losses in the electromagnetic drive,
$L_S$=inductance of driving coil,
$u_{ind}$=velocity-proportional induction voltage on the coil,
v=velocity of the measuring tube,
m=vibrating mass of the measuring tubes and of the measurement medium (effectively vibrating mass),
c=system stiffness of the measuring tubes and of the measurement medium (effective system stiffness),
d=attenuation coefficient of the measuring tubes and of the measurement medium (process-dictated attenuation) and
$F_m$=driving force.

The resistance $R_S$ describes the ohmic resistance of the driving coil which is encompassed by the electromagnetic drive 4. The resistance $R_W$ describes the eddy current losses in the electromagnetic vibration generator and the inductance of the driving coil is described by $L_S$. For assessing the state of motion of the resonance measurement system 1, the phase angle between the current $i_L$ through the inductance $L_S$ and the velocity of the vibrating element 5 is of interest. The current $i_L$ which is flowing exclusively through the inductance $L_S$ causes a proportional force action $F_m$ on the vibrating element 5. It is immediately apparent from the equivalent circuit diagram as shown in FIG. 6 that the current $i_L$ need not be in phase with the driving terminal current $i_{DrA}$.

To compute the complex load according to equation (1), the following equations can be derived from FIG. 6:

$$u_{DrA} = R_S i_{DrA} + R_W i_W \quad (2)$$

$$u_{DrA} = R_S i_{DrA} + L_S \frac{di_L}{dt} + u_{ind}$$

$$i_{DrA} = i_L + i_W$$

$$F_m = m\dot{v} + dv + c\int v d\tau$$

$$F_m = k i_L$$

$$u_{ind} = kv$$

The component mathematical models for the electromagnetic drive 4 and the vibrating element 5 are coupled to one another by the transfer coefficient k, equally a proportionality existing between the current $i_L$ through the coil in the equivalent circuit diagram with the inductance $L_s$ and the force action $F_m$ which has been caused thereby, on the one hand, and on the other hand, between the velocity v of the measuring tube as the vibrating element 5 and the reaction which has been generated thereby in the form of the induced voltage $u_{ind}$. Since the two actions are generated by the same electromagnetic drive 4, the same transfer coefficient k, in fact, applies to both equations. The transfer coefficient k is not absolutely necessary for the determination of many quantities of interest as an absolute value, because often only relations of values to one another are considered because certain values are of interest only with respect to their phase angle, less in terms of their amount, and because in practice corresponding values for k can be determined in an initial calibration. Likewise, it is of course possible to specify an exact value for k even if the determination also means a certain measurement engineering effort.

Depending on whether the electrical actuating apparatus at its output drives a current or a voltage and accordingly sets either the driving terminal current $i_{DrA}$ or the driving terminal voltage $u_{DrA}$ as the output quantity $u_2$, the transfer functions are different. For the case in which the driving terminal current $i_{DrA}$ is set to a driving terminal voltage $u_{DrA}$ which has been delivered by the electrical actuating apparatus (U-U power amplifier), the load admittance in the map region that arises as a reaction can be described by the following equation (3):

$$\frac{I_{DrA}}{U_{DrA}} = G = \quad (3)$$

$$\frac{1}{(R_S + R_W)} \cdot \frac{L_S m s^3 + (L_S d + R_W m)s^2 + (L_S c + R_W d + k^2)s + R_W c}{L_S m s^3 + (L_S d + (R_W \| R_S)m)s^2 + (L_S c + k^2 + (R_W \| R_S)d)s + (R_W \| R_S)c}$$

For the case in which the electrical actuating apparatus 3 drives the driving terminal current $i_{DrA}$ and the driving terminal voltage arises as the reaction, for the complex load resistance (electrical actuating apparatus 3 works as an U-I power amplifier), the following arises:

$$\frac{U_{DrA}}{I_{DrA}} = Z = \quad (4)$$

$$(R_S + R_W) \cdot \frac{L_S m s^3 + (L_S d + (R_W \| R_S)m)s^2 + (L_S c + k^2 + (R_W \| R_S)d)s + (R_W \| R_S)c}{L_S m s^3 + (L_S d + R_W m)s^2 + (L_S c + R_W d + k^2)s + R_W c}.$$

The two transfer functions describe the complex load admittance $\underline{G}$ and the complex load resistance $\underline{Z}$ with which the electrical actuating apparatus is loaded altogether, therefore electrically, mechanically and flow-mechanically, hereinafter designated simply G and Z. The parameters of the transfer functions can be identified in a very different manner, for example, by the transfer functions being examined at different frequencies and at these frequencies measured values for the driving terminal current $i_{DrA}$ and the driving terminal voltage $u_{DrA}$ being detected and being used for evaluation of the equations, and thus, of the mathematical model 8.

The transfer functions according to equations 3 and 4 describe the complex load admittance G and the complex load resistance Z with which the power part of the sensor electronics, therefore the electrical actuating apparatus 3, is altogether loaded. The load is composed of electrical, mechanical and flow-mechanical components. The active power is converted in the real part of the complex load and is composed of the losses in the ohmic resistance of the driving coil and eddy current losses, of mechanical losses by material damping and friction, and of flow-induced losses.

For purposes of illustration, the indicated relationships for the complex load admittance G and the complex load resistance Z—therefore the complex load—are simplified by the eddy currents being ignored:

$$R_W \to \infty \Rightarrow \frac{I_{DrA}}{U_{DrA}} = \quad (5)$$

$$\frac{ms^2 + ds + c}{L_S m s^3 + (L_S d + R_S m)s^2 + (L_S c + k^2 + R_S d)s + R_S c}$$

$$\frac{I_{DrA}}{U_{DrA}} = \frac{1}{L_S s + R_S + \frac{k^2 s}{ms^2 + ds + c}}$$

and $$\frac{U_{DrA}}{I_{DrA}} = R_S + sL_S + \frac{k^2 s}{(ms^2 + ds + c)}$$

The equation becomes still more descriptive when the load is examined at the working point, i.e., when the operating frequency corresponds to the resonant frequency of the first natural mode of the measuring tube:

$$\omega_0 = \sqrt{\frac{c}{m}} \Rightarrow ms^2 + c = 0 \Rightarrow \quad (6)$$

$$\frac{I_{DrA}}{U_{DrA}} = \frac{1}{jL_S\omega_0 + R_S + \frac{k^2}{d}} = \frac{1}{jL_S\omega_0 + R_S + \frac{k^2}{d_0 + \Delta d}}$$

and

-continued
$$\frac{U_{DrA}}{I_{DrA}} = R_S + j\omega_0 L_S + \frac{k^2}{d} = R_S + j\omega_0 L_S + \frac{k^2}{d_0 + \Delta d}$$

Here, $d_0$ is the attenuation constant of the sensor without the measuring medium flowing through the measuring tube. With the measuring medium the attenuation constant changes by $\Delta d$ for example, as a result of the viscosity or as a result of the secondary flow in multiphase flows. The change of the attenuation constant and thus of the load can be several powers of ten especially in multiphase flows.

The voltage $U_{DrA}$ and $u_{DrA}$ and the current $I_{DA}$ and $I_{DrA}$ at the output of the power amplifier are phase-selectively measured via preamplifier, multiplexer, amplifier, A/D converter and DSP. The complex load resistance Z and the complex load admittance G are determined from them.

The equation relationships shown above facilitate the understanding of which factors play a part for the actual loading of the electromagnetic drive 4 and are included in the complex load admittance G and the complex load resistance Z, altogether therefore play a part in the complex load.

The above described method for operation of the resonance measurement system 1 is preferably carried out by the complex load admittance G or complex load resistance Z with which the electrical actuating apparatus 3 is loaded being determined from the measured driving terminal current $i_{DrA}$ and from the measured driving terminal voltage $u_{DrA}$, and using the complex load admittance G and/or complex load resistance Z, the limit value $u_{2-B}$ being determined for the electrical excitation signal $u_2$. How accurately the determination is made depends on which type the electrical actuating apparatus 3 it is.

For the case in which the electrical actuating apparatus 3 works as a controlled voltage source, it is necessarily possible to act only in a dedicated manner on the driving terminal voltage $u_{DrA}$ so that here the desired power limitation can be achieved via a voltage boundary value so that the resonance system 1 works altogether in the linear range. This can be achieved in that a voltage boundary value $u_{DrA-BI}$ is computed as a limit value $u_{2-B}$ from the complex load admittance G or the complex load resistance Z, on the one hand, and on the other hand, from the maximum driving terminal current $i_{DrA-max}$, and/or a voltage boundary value $u_{DrA-BS}$ is computed as a limit value $u_{2-B}$ from the maximum driving power $S_{DrA-max}$. Preferably, both the voltage boundary value $u_{DrA-BI}$ is computed as the limit value $u_{2-B}$ and the voltage boundary value $u_{DrA-BS}$ is computed as the limit value $u_{2-B}$, and the smaller of the two values is used as a limit value $u_{2-B}$ for the electrical excitation signal $u_2$. The process is described as follows by the following equation:

$$\left. \begin{array}{c} I_{DrA} > I_{DrA-max} \\ \vee \\ S_{DrA} = I_{DrA} U_{DrA} > S_{DrA-max} \end{array} \right\} \Rightarrow \tag{7}$$

$$Z = \frac{U_{DrA}}{I_{DrA}} \Rightarrow \begin{cases} U_{DrA-BI} = Z \cdot I_{DrA-max} \\ U_{DrA-BS} = \sqrt{Z \cdot S_{DrA-max}} \end{cases} \Rightarrow$$

$$\Rightarrow \begin{cases} U_{DrA-BI} > U_{DrA-BS} \Rightarrow U_{DrA} = U_{DrA-BS} \\ U_{DrA-BI} < U_{DrA-BS} \Rightarrow U_{DrA} = U_{DrA-BI} \end{cases}$$

The indicated equations (7) apply only if the current limitation or the power limitation takes effect, otherwise the values are retained for adjustment, in particular, for amplitude adjustment of the deflection of the measuring tubes.

For the case in which the electrical actuating apparatus 3 is working as a controlled voltage source, it is necessarily possible to act only in a dedicated manner on the driving terminal current $i_{DrA}$ so that here the desired power limitation can be achieved via a current boundary value so that the resonance system 1 works altogether in the linear range. This can be achieved in that a current boundary value $i_{DrA-BI}$ is computed as a limit value $u_{2-B}$, on the one hand, from the complex load admittance G or the complex load resistance Z, and on the other hand, from the maximum driving terminal voltage $u_{DrA-max}$, and/or a current boundary value $i_{DrA-BS}$ is computed as a limit value $u_{2-B}$ from the maximum driving power $S_{DrA-max}$. Preferably, both the current boundary value $i_{DrA-BI}$ is computed as the limit value $u_{2-B}$ and the current boundary value $i_{DrA-BS}$ is computed as the limit value $u_{2-B}$, and the smaller of the two values is used as a limit value $u_{2-B}$ for the electrical excitation signal $u_2$. The computation takes place analogously to equation group 7.

Figure 7:
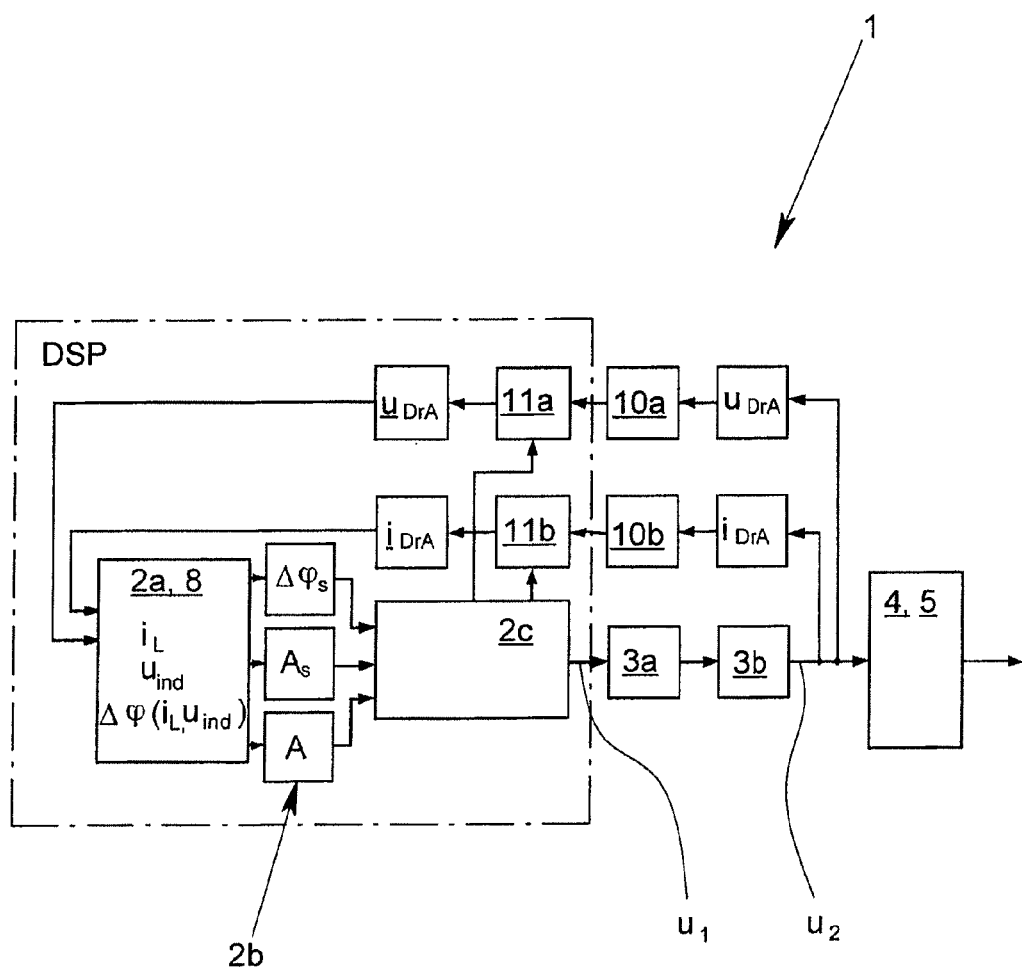
FIG. 7 shows an exemplary embodiment of the inventive method for operating a resonance measurement system in a block circuit diagram and FIG. 8 shows a schematic of the behavior of the driving terminal voltage and the driving terminal current for current limitation, voltage limitation and power limitation.

One especially elegant possibility for limiting the electrical excitation signal $u_2$ to the limit value $u_{2-B}$ arises by a matched, especially smaller set point for the amplitude being specified for an amplitude adjustment for adjusting the amplitude of the vibrating element. FIG. 7 schematically shows the implementation of a control circuit for operation of the resonance measurement system 1. The resonance measurement system 1 is shown in the form of a Coriolis mass flow meter, the resonance measurement system 1 having a controller 2 which has been implemented in a digital signal processor (DSP), as well as an electrical actuating apparatus 3 with a digital/analog converter 3a and a voltage-controlled voltage source 3b as the power part. The electromagnetic drive 4 has a coil which deflects the vibrating element 5 and excites it to vibration. In the illustrated exemplary embodiment the electrical excitation signal $u_2$ which has been generated by the electrical actuating apparatus 3 is a voltage which is equal to the driving terminal voltage $u_{DrA}$ of the electromagnetic drive 4. The driving terminal current $i_{DrA}$ is consistently established according to the impressed voltage $u_{DrA}$, according to the parameters of the electromagnetic drive 4 and of the vibrating element 5, and according to the state of motion of the vibrating element 5 in conjunction with the medium. The driving terminal voltage $u_{DrA}$ and the driving terminal current $i_{DrA}$ are, in any case, acquired using measurement engineering and are converted with analog/digital converters 10a, 10b.

FIG. 7 shows the controller 2 broken down. In the controller part 2a, a mathematical model 8 is filed so that, here, all computations which relate to the model 8 can take place. The method of the invention is, however, not tied to the use of a complicated mathematical model 8, rather the method can also be used with control circuits without a model. In the controller parts 2b, the actual controllers are implemented at the top, for example, for phase adjustment, in the middle for amplitude adjustment and at the bottom for amplitude control. Outputs of the controllers 2b are manipulated variables which are converted by the signal generator 2c. To excite the vibrating element 5 in the signal generator 2c, first, two orthogonal harmonic excitation signals are generated, from which, together, the controller output signal $u_1$ is generated. The likewise harmonic measured variables which are supplied again to the DSP via the analog/digital converters 10a, 10b are broken down into signal components in the demodulators 11a, 11b using the orthogonal base signals of the signal generator 2c which allow the determination of the phase angle of the signals with reference to the base signal so that, after demodulation, there is phase information relative to the output signal of the signal generator 2c. The driving terminal voltage $U_{DrA}$ which is known in amount and phase and the driving terminal current $i_{DrA}$ are then evaluated together in the controller such that the set point $A_S$ for the amplitude is matched and the determined voltage boundary value $u_{DrA-BI}$ and $U_{DrA-BS}$ is maintained.

Figure 8:
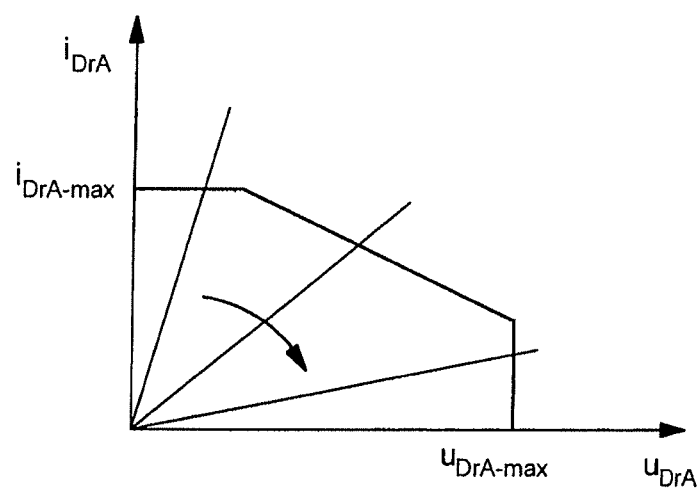

Finally, FIG. 8 shows that the electrical actuating apparatus 3 is operated such that the driving terminal current $i_{DrA}$ produced is always smaller than the specified maximum driving terminal current $i_{DrA-max}$ and that the driving terminal voltage $u_{DrA}$ which has been produced is always smaller than the specified maximum driving terminal voltage $u_{DrA-max}$ and that the driving power $S_{DrA}$ is always smaller than the specified maximum driving power $S_{DrA-max}$. The characteristic for the power limitation is shown linearly here, simplified. The curved arrow indicates the direction of the working line with increasing load. At low loads the current boundary value is defining, at very high loads the voltage limit is limiting, in the working range of the resonance measurement system between these two situations the power which can be delivered at maximum by the electrical actuating apparatus 3 is limiting.

What is claimed is:

1. A method for operating a resonance measurement system having at least one electrical actuating apparatus, at least one electromagnetic drive as a vibration generator and at least one vibrating element which interacts with a medium, comprising the steps of:
   causing the electrical actuating apparatus to provide an electrical excitation signal $u_2$ for excitation of the electromagnetic drive,
   exciting the vibrating element to vibration in at least one natural form with the electromagnetic drive,
   producing a driving terminal current $i_{DrA}$ by the electrical excitation signal $u_2$,
   producing a driving terminal voltage $u_{DrA}$ of the electromagnetic drive by the electrical excitation signal $u_2$,
   detecting the driving terminal current $i_{DrA}$ and the driving terminal voltage $u_{DrA}$,
   determining a driving power $S_{DrA}$ from the driving terminal current $i_{DrA}$ and driving terminal voltage $U_{DrA}$,
   when at least one of a given maximum driving terminal current $i_{DrA-max}$ is exceeded by the driving terminal current $i_{DrA}$, a given maximum driving terminal voltage $u_{DrA-max}$ is exceeded by the driving terminal voltage $u_{DrA}$, and a given maximum driving power $S_{DrA-max}$ is exceeded by the driving power $S_{DrA}$, the electrical excitation signal $u_2$ is limited to a limit value $u_{2-B}$ by which, respectively, at least one of the driving terminal current $i_{DrA}$ remains below a given maximum driving terminal current $i_{DrA-max}$, the driving terminal voltage $u_{DrA}$ remains below a given maximum driving terminal voltage $u_{DrA-max}$ and the driving power $S_{DrA}$ remains below a maximum driving power $S_{DrA-max}$.

2. The method as claimed in claim 1, wherein from the measured driving terminal current $i_{DrA}$ and from the measured driving terminal voltage $u_{DrA}$, at least one of a complex load admittance G and a complex load resistance Z with which the electrical actuating apparatus is loaded is determined, and based on at least one of the complex load admittance G and the complex load resistance Z, the limit value $u_{2-B}$ for the electrical excitation signal is determined.

3. The method as claimed in claim 1, wherein the limitation of the electrical excitation signal $u_2$ to the limit value $u_{2-B}$ takes place by a matched set point for the amplitude being specified for adjusting the amplitude of the vibrating element.

4. The method as claimed in claim 2, wherein the electrical actuating apparatus works as a controlled voltage source and the voltage boundary value $U_{DrA-BI}$ is computed as a limit value $u_{2-B}$ from one of the complex load admittance G and the complex load resistance Z and wherein a limit value $u_{2-B}$ is computed as a maximum driving power $S_{DrA-max}$ from at least one of the maximum driving terminal current $i_{DrA-max}$, and a voltage boundary value $u_{DrA-BS}$.

5. The method as claimed in claim 4, wherein both the voltage boundary value $u_{DrA-BI}$ is computed as the limit value $u_{2-B}$ and the voltage boundary value $u_{DrA-BS}$ is computed as the limit value $u_{2-B}$, and the smaller of the two values is used as a limit value $u_{2-B}$ for the electrical excitation signal $u_2$.

6. The method as claimed in claim 2, wherein the electrical actuating apparatus works as a controlled voltage source and a current boundary value $i_{DrA-BU}$ is computed as a limit value $u_{2-B}$ from one of the complex load admittance G and the complex load resistance Z and wherein at least one of the maximum driving terminal voltage $u_{DrA-max}$, and a current boundary value $i_{DrA-BS}$ is computed as a limit value $u_{2-B}$ from the maximum driving power $S_{DrA-max}$.

7. The method as claimed in claim 4, wherein both the current boundary value $i_{DrA-BU}$ is computed as the limit value $u_{2-B}$ and the current boundary value $i_{DrA-BS}$ is computed as the limit value $u_{2-B}$, and the smaller of the two values is used as a limit value $u_{2-B}$ for the electrical excitation signal $u_2$.

8. The method as claimed in claim 1, wherein the electrical actuating apparatus is operated such that the driving terminal current $i_{DrA}$ is always smaller than the specified maximum driving terminal current $i_{DrA-max}$, wherein the driving terminal voltage $u_{DrA}$ is always smaller than the specified maximum driving terminal voltage $U_{DrA-max}$, and wherein the driving power $S_{DrA}$ is always smaller than the specified maximum driving power $S_{DrA-max}$.

* * * * *